United States Patent [19]
ter Meulen et al.

[11] Patent Number: 5,646,032
[45] Date of Patent: Jul. 8, 1997

[54] RECOMBINANT FOAMY VIRUS VECTORS FOR MEDICINAL, AND DIAGNOSTIC USES, AND PROCESSES FOR PREPARING RECOMBINANT FOAMY VIRUS VECTORS

[75] Inventors: Volker ter Meulen, Rimpar; Axel Rethwilm, Würzburg, both of Germany

[73] Assignee: Bayer Aktiengesellschaft, Leverkusen, Germany

[21] Appl. No.: 345,278

[22] Filed: Nov. 28, 1994

Related U.S. Application Data

[63] Continuation of Ser. No. 249,509, May 26, 1994, abandoned.

[30] Foreign Application Priority Data

Jun. 3, 1993 [DE] Germany ............ 43 18 387.5

[51] Int. Cl.$^6$ ............ C12N 5/16; C12N 15/86
[52] U.S. Cl. ............ 435/325; 435/320.1; 435/366; 435/372; 435/352; 435/350; 435/364; 435/358; 435/357
[58] Field of Search ............ 435/172.1, 172.3, 435/320.1, 240.1, 240.2; 536/23.1, 23.72

[56] References Cited

PUBLICATIONS

Rethwilm et al. "Transacting Transcriptional Activation of Human Spumaretrovirus LTR in Infected Cells", Virology, vol. 175, 1990, pp. 568–571.
Netzer et al. "Identification of Pol–Related Gene Products of Human Foamy Virus", Virology, vol. 192, 1993, pp. 336–338.
Bothe et al. "Progressive Encephalopathy and Myopathy in Transgenic Mice Expressing Human Foamy Virus Genes", Science, vol. 253, 2 Aug. 1991, pp. 555–557.
D. Jolly, Cancer Gene Therapy, 1: 51–64 (1994).
J.M. Coffin, "Retroviridae and their Replication", in Virology, 2nd ed., pp. 1437–1440.
J.J. Hooks et al., Bacteriol. Rev., 39: 169–185 (1975).
J.J. Hooks et al., "Spumavirinae: Foamy Virus Group Infections: Comparative Aspects and Diagnosis", in Comparative Diagnosis of Viral Diseases, 4: 599–618 (1981).
D. Neumann–Haefelin et al., Intervirology, 35: 196–207 (1993).
P. Loh, "Spumaviruses", in The Retroviridae, 2: 361, Plenum Press, New York, 1993.

M. Schweizer et al., AIDS Research and Human Retroviruses, 10: 601–605 (1994).
M. Schweizer et al., AIDS Research and Human Retroviruses, 11: 161–170 (1995).
R. Weiss, Nature, 333: 497–498 (1988).
M. Schmidt et al., Virology, 210: 000–000 (in press).
O. Erlwein et al. et al., Virology, 196: 256–268 (1993).
G. Braunach et al., J. Virology, 67: 5411–5418 (1993).
L. Hong et al., Virus Research, 30: 89–95 (1993).
A. D. Miller et al., PNAS, 80: 4709–4713 (1983).
A. Kasid et al, PNAS, 87:473–477 (1990).
J. M. Wilson et al., Science, 248: 1413–1416 (1990).
S. A. Rosenberg et al., Human Gene Therapy, 3: 57–73 (1992).
B. Gansbacher et al., Human Gene Therapy, 3: 691–703 (1992).
B. Gansbacher et al., Human Gene Therapy, 3: 677–690 (1992).
M. T. Loetz et al., Human Gene Therapy, 5: 41–55 (1994).
H. Fakhrai et al., Human Gene Therapy, 6: 591–601 (1995).
Genzyme Diagnotics Catalog (1994), pp. 1, 43, 59.
J. Larrick et al., Gene Therapy: Application of Molecular Biology, Elsevier, New York, 1991, pp. 77–84.
A. D. Miller et al., Biotechniques, 7: 980–990 (1989).
R. M. Flügel et al., Embo J. 6, 2077–2084 (1987).
B. Maurer et al., J. Virol. 62, 1590–1597 (1988).
A. Rethwilm et al., Nucleic Acids Res. 18, 733–738 (1990).
A. D. Miller et al., Biotechniques 7, 980–990 (1989).
A. Rethwilm et al., Gene 59, 19–28 (1987).
A. Rethwilm et al. Nucleic Acids Research, vol. 18, No. 4, 1990, pp. 733–738.
Vile et al. Virology, vol. 189, No. 2, Aug. 1992, pp. 786–791.
Maurer et al. Journal of Virology, vol. 65, No. 11, Nov. 1991, pp. 6353–6357.
Lee et al. Journal of Virology, vol. 67, No. 4, Apr. 1993, pp. 2317–2326.

Primary Examiner—David Guzo
Attorney, Agent, or Firm—Sprung Horn Kramer & Woods

[57] ABSTRACT

The present invention relates to the preparation of novel vector systems which are generated by in-vitro recombination, using gene technology, of nucleic acids from foamy virus species and of exogenous nucleic acid, and are produced by suitable host cells or by recombinantly altered packaging cell lines. The recombinant preparation of particularly suitable packaging cell lines is likewise a constituent of this invention. The invention is distinguished by the safe and efficient transfer by foamy virus vectors of therapeutic and other genes into eukaryotic cells.

19 Claims, 7 Drawing Sheets

RECOMBINANT FOAMY VIRUS VECTORS FOR MEDICINAL, AND DIAGNOSTIC USES, AND PROCESSES FOR PREPARING RECOMBINANT FOAMY VIRUS VECTORS

This application is a continuation, of application Ser. No. 08/249,509, filed on May 26, 1994 abandoned.

The present invention relates to the preparation of novel vector systems which are generated by in-vitro recombination, using gene technology, of nucleic acids from foamy virus species and of exogenous nucleic acid, and are produced by suitable host cells or by recombinantly altered packaging cell lines. The recombinant preparation of particularly suitable packaging cell lines is likewise a constituent of this invention. The invention is distinguished by the safe and efficient transfer by foamy virus vectors of therapeutic and other genes into eukaryotic cells.

The foamy virus vectors reach an extremely broad spectrum of eucaryotic cells: they transduce a very wide variety of mammalian cells; they can be used, in particular, for transferring genes into many different somatic cells in humans.

The foamy virus vectors are distinguished by a large capacity for accepting exogenous DNA fragments.

The expression of exogenous DNA in the foamy virus vectors can be regulated stringently, for example, by the viral transactivator bel-1, if no exogenous promoter is used in the vector.

The foamy virus vectors derived from foamy virus are non-pathogenic in humans and are therefore safe to use. There is no evidence that human foamy virus causes pathological effects in man. Former reports speculating that human foamy virus is involved in neurological diseases, Graves' disease, other autoimmune conditions, thyroiditis de Quervain, or amyotrophic lateral sclerosis can now clearly be denied on the basis of intensive analyses for foamy virus in such clinical samples. Safety of foamy virus vectors for use also derives from the fact that homologous DNA sequences, which can give rise to homologous recombination of foamy virus vector and cellular DNA, are not present in human chromosomal DNA. Foamy viruses are phylogentically distinct from other retroviruses.

Foamy virus, and the vectors derived from it, have no known oncogenic potential.

Replication-competent foamy virus vectors are prepared, inter alia, by deleting the viral genes bel-2 and bel-3.

For example, the foamy virus vectors pFOV-1, pFOV-2 and pFOV-3 possess in common a deletion of about 420 base pairs in the 3' direction adjoining the bel-1 gene.

In addition, replication-incompetent foamy virus vectors, such as, for example, pFOV-4, were prepared which can be produced in packaging cell lines which are likewise prepared by gene technology.

Foamy virus vectors are suitable for expressing exogenous DNA in human or animal target cells in order to form therapeutically active proteins or antisense RNA or decoy RNA. Foamy virus vectors are suitable for expressing exogenous DNA in humans or animals in order to produce humoral immunity and/or cellular immunity.

By means of selecting the exogenous nucleic acid of the vector, foamy virus vectors may suitably be used for inactivating undesirable genes, by homologous recombination, in the chromosomal DNA of the target cells in humans or animals, or for complementing gene deficiencies.

By virtue of regulating the expression of a reporter gene in the target tissue, or by means of other gene constructions, foamy virus vectors are suitable for use as diagnostic agents.

Human foamy virus (HFV) belongs to the Spumavirus family of the retroviruses. The Spumavirus family of the retroviruses differs clearly from other retroviruses [R. M. Fl ügel et al., EMBO J. 6, 2077–2084 (1987); B. Maurer et al., J. Virol, 62, 1590–1597 (1988); A. Rethwilm et al., Nucleic Acids Res. 18, 733–738 (1990)].

It is of particular importance for the present invention that HFV isolates have not as yet been shown to be pathogenic in humans. Since HFV furthermore transduces a multiplicity of different cell types in human tissue, vectors were developed as "gene-delivery systems", which derive from the infectious molecular clone pHSRV [A. Rethwilm et al., Nucleic Acids Research 18, 733–738 (1990)] and are the subject of the present invention. In its use as a vector for "gene delivery", foamy virus is novel.

HFV vectors differ fundamentally from other retrovital vectors, such as, for example, MoMLV (Moloney murine leukosis virus), from which the widely disseminated N2 vectors [A. D. Miller et al., Biotechniques 7, 980–990 (1989)] are derived, in that HFV is not known to have any oncogenic potential and HFV vectors must be presumed to be safe for use. In addition, foamy viruses have access to an extremely broad host spectrum, which includes fibroblastoid, epitheloid and lymphatic cells. Furthermore, HFV derivatives represent safe vectors owing to the fact that the presence of the viral transactivator bel-1 is mandatory if the foamy virus LTR (long terminal repeat) is to be transcriptionally active. If, however, the vector does not contain the genetic information for the bel-1 transactivator, no mobilizable, replication-competent HFV vector, e.g. with oncogenic potential, can be produced in the cell because the LTR sequence does not activate transcription without a transactivating bel-1 gene. Activation of cellular oncogenes by insertion mutagenesis is likewise improbable. A further safety factor in using HFV derivatives as vectors is that endogenous homologues of foamy viruses are unknown and there cannot therefore be any question of recombination with endogenous retroviruses. This observation is also of importance for the particularly high degree of genetic stability of foamy virus vectors in use.

Recombinant foamy viruses, as described, for example, in the construction examples for pFOV-1 to pFOV-4 given below, are suitable for transferring genetic material into permanent animal or human cell lines or into somatic cells in humans or animals. They represent a vector for introducing hereditary information into eukaryotic cells which possess advantages over conventional gene-transfer systems (MoMLV, adenoassociated virus or sindbis virus, or formulations of DNA with adenovirus particles, detergents and other additives, or physical methods) in the range of possible applications, in the efficacy of gene transfer into the target cells and in safety of handling.

Thus, the foamy virus vectors which are mentioned in the example experiments, and which possess a multiple cloning sequence for inserting exogenous nucleic acids in the region of the bel-1 or bel-2 gene, can be used for the purposes stated below. However, it is also possible to make other deletions in the provital DNA of pHFV or other foamy virus isolates in order to insert a multiple cloning sequence and thereby construct alternative foamy virus vectors.

Since such recombinant foamy virus vectors are able to accept an exogenous nucleic acid (DNA fragment) which can easily exceed 1700 base pairs in length, such foamy virus vectors can introduce an expressible, exogenous DNA for a multiplicity of possible applications into cell lines for production purposes or into somatic cells for medicinal or diagnostic purposes:

1. Foamy virus vectors for vaccination

The exogenous nucleic acid in a recombinant foamy virus vector can comprise one or more complete genes for expressing one or more polypeptides. Such peptides can be suitable, following their expression by this foamy virus vector in transduced target cells, for eliciting humoral and/or cellular immunity in humans or animals. It has been shown that it is in particular polypeptide which has been formed intracellularly which is of importance for eliciting cellular immunity (J. B. Ulmer et al., Science 259, 1745–1749 (1993)).

Foamy virus vectors which carry exogenous nucleic acid and which encode, and express in transduced somatic target cells, the vital proteins of HIV, HTLV, hepatitis B, hepatitis C, human papilloma virus, cytomegatovirus, HSV or influenza virus, or animal herpesviruses, such as, for example, PRV, BHV or EHV, or other viruses, can represent potent vaccines which can be employed prophylactically or as a therapeutic procedure following infection of humans or animals by a pathogenic virus.

Furthermore, foamy virus vectors can be employed in accordance with the same principle for vaccinating against bacterial infections, against mycoplasma infections or against infections by plasmodias or other endoparasites. For such vaccinations replication-incompetent but infectious foamy virus vector particles of a titer of $10^3$ to $10^7$ or more particles per milliliter aqueous buffer solution is injected subcutaneously or intramuscularly for in vivo transduction of cells. Otherwise, fibroblasts, myoblasts or other somatic cells are transduced ex vivo by co-cultivating such cells with foamy virus producing cells or by incubating somatic cells of interest with buffered aqueous suspensions containing titers of foamy virus vector in the range of $10^3$–$10^7$ or more particles per milliliter.

II. Foamy virus vectors for expressing therapeutic RNA, in particular for the therapy of viral diseases and cancerous diseases The exogenous nucleic acid in recombinant foamy virus vectors can comprise one or more genes which, in transduced cells, express RNA which possesses a complementary (antisense)nucleotide base sequence to that of undesirable RNA molecules in the target cell, or else possesses nuclease-active ribozyme RNA.

These undesirable RNA molecules can be the genomic RNA of lentiviruses or of other RNA viruses. They can also be the messenger RNA molecules of intracellular pathogens such as lentiviruses (HIV, HTLV, inter alia), hepatitis B viruses, hepatitis C viruses, human papilloma viruses, cytomegaloviruses, Epstein-Barr viruses, herpes simplex viruses, herpesviruses of animals (PRV, BHV and EHV, for example), or other pathogenic viruses or mycoplasmas, or intracelluiarly replicating prokaryotes.

However, the undesirable RNA molecules can also be mRNA transcripts of oncogenes or of other genes which contribute causatively to the malignant growth of somatic cells. Thus, foamy virus vectors expressing antisense RNA against the c-myc RNA transcript, for example, would be employed in the case of malignant disorders such as Burkitt's lymphoma. The undesirable RNA molecules can also encode proteins which participate causatively in the genesis or manifestation of autoimmune disorders or metabolic disorders. Using complementary antisense RNA, which can be encoded by a recombinant foamy virus vector, such undesirable RNA molecules can be inactivated in transduced cells in a sequence-selective manner by Watson-Crick base pairing. Foamy virus vectors can therefore be used in infected or pathologically altered cells for the therapy, employing antisense RNA expression, of infectious diseases caused by bacteria, viruses and other organisms, and of cancerous or autoimmune diseases.

The antisense RNA or ribozyme RNA expressed using foamy virus vectors can also be directed against other genes which are involved in metabolic disorders or neurodegenerative disorders. Thus, the inactivation, using antisense RNA or ribozyme RNA expressed by foamy virus vectors, of mRNA encoding Alzheimer's β-amyloid protein precursor or acetylcholinesterase in neuronal tissue can also be of therapeutic value.

Instead of exogenous nucleic acid encoding antisense RNA, an exogenous nucleic acid can be inserted into recombinant foamy virus vectors which are to be used therapeutically which encodes a decoy RNA.

Decoy RNA can display a strong antiviral effect and be employed, for example, for treating viral infections.

For this purpose, the decoy RNA contains particular nucleotide base sequences which, for their part, bind virus proteins which are essential for the replication of a pathogenic virus. Thus, decoy RNA sequences can, for example, contain multiple copies of the TAR nucleotide base sequence and the REV responsive element nucleotide base sequence (RRE) from HIV and competitively bind the tat and rev regulatory proteins of HIV, and thereby lower the rate of replication of HIV in the infected cell. This signifies a therapeutic antiviral effect.

However, the decoy RNA can also contain the packaging sequence from lentiviruses, as described for HIV, for example, in the genomic RNA between the 5'-LTR and extending into the gag sequence.

Using foamy virus vectors for delivery of therapeutic nucleic acids into somatic cells of interests, two different methods for ex vivo or in vivo foamy virus application can be applied, in general: For ex vivo transduction of a sample of somatic cells containing the cells to be transduced, these cells can be co-cultivated together with a foamy virus vector producing cell line in an appropriate cell culture medium for certain periods of incubation time. Usually, incubation time for ex vivo transduction is 4 hours to 36 hours. Conditions of co-cultivation are choosen that allow efficient transduction of target cells and that also allow separation of target cells and foamy virus vector producing cell line after incubation to reinject or reinfuse transduced somatic cells. The techniques for ex vivo transduction of somatic cells for clinical applications are well established in case of retrovital gene transfer. Such techniques which are reported in detail in the scientific literature can also be applied for transduction of cells by foamy virus vectors (for review see Richard C. Muliigan: "The Basic Science of Gene Therapy" in: Science. Vol. 260, 926–932, 1993); W. French Anderson: "Human Gone Therapy" in: Science, Vol. 256, 808–813, 1992; A. Dusty Miller: "Human gone therapy comes of age"in: Nature, Vol. 357, 455–460, 1992).

For in vivo transduction of somatic cells using foamy virus vector a buffered aqueous suspension containing $10^3$–$10^7$ or more foamy virus vector particles per milliliter is injected into the tissue containing the target cells to be transduced. Foamy virus vector containing suspensions of a volume of 1 μl–1 ml or more can be injected into different tissues in vivo. That is, inter alia, bone marrow, liver, blood, lymph nodes, skeleton muscle, skin epidermal tissue, skin fibroblast tissue, brain, thymus, or other organs. In vivo transduction can be conducted by non-invasive foamy virus vector applications like topical administration of foamy virus vector containing formulations including pastes or creams, or by aerosols, foams or powder formulations for inhalation.

For generation of foamy virus vector for ex vivo and in vivo application it has also to be mentioned that so called pseudotypes of these vector particles can be used. Pseudotype foamy virus vectors are generated by genetically altered packaging cell lines, or by using production cell lines intentionally infected by a virus like Vesicula stomatitis virus or by replication-incompetent HIV or other viruses that express proteins like envelope glycoproteins. These foreign vital proteins can be taken up into the foamy virus vector protein coat to form a heterogeneously composed envelope of the vector. Such pseudotype vectors exert for certain applications advantages. They can be used for increasing foamy virus vector particle concentraion in the supernatant of packaging cells. They can also be used to extend host range of the foamy virus vector particle. In particular, pseudotype foamy virus vectors carrying HIV envelope protein is of interest to direct the vector specifically to target cells expressing CD4 receptor. Likewise, pseudotype foamy virus vectors preferentially directed by heterologous envelope proteins to other cell types like liver cells using Hepatitis virus proteins or Rhinovirus proteins for targetting ICAM-1 expressing cells, for instance, are of interest. Additionally to this advantage, heterologous proteins like HIV envelope protein in pseudotype foamy virus vector elicit desirable immune responses.

III. Foamy virus vectors for expressing polypeptides for the therapy of vital, cancerous and autoimmune diseases The exogenous nucleic acid in a recombinant foamy virus vector can comprise one or more genes for expressing polypeptides. If these polypeptides are expressed in the target cell transduced by the vector, they can be regulatory proteins which act in a transdominantly negative manner and retard the rate of replication of a pathogenic virus, and therefore have an antiviral effect. Regulatory proteins acting in a transdominantly negative manner are, for example, proteins which interfere with the assembly of virus particles or represent an alternated tat protein or rev protein of HIV.

While these altered proteins still bind to the TAR or RRE sequence of HIV RNA, their biological function, namely the antitermination of transcription (the tat function) or the RNA-processing function of rev, is no longer expressed, owing to a mutation in the non-binding part of the protein.

Other antiviral polypeptides having a therapeutic effect in virus diseases are those which resemble the receptor for internalizing the pathogenic virus at the virus binding site. Using a foamy virus vector, polypeptides can be expressed and secreted in the organism which bind to that binding site of the pathogenic virus which is of importance for binding the virus to the cellular receptor, and thus block uptake of the virus into the cell. In this connection, a foamy virus vector could be therapeutically effective which expresses a CD4 polypeptide fragment which, by binding to HIV gp 120, prevents the de-novo infection of human cells by HIV.

In a similar manner, the peptide formed with the aid of recombinant foamy virus vector could represent a soluble moiety of a growth factor receptor and capture over expressed growth factor which is leading to malignant cell growth. By these means, the foamy virus vector would be expressing anti-tumour properties.

This principle could also be used for treating autoimmune diseases. Two examples may be mentioned in this connection:

1. For the purposes of immune suppression, and for preventing organ transplant rejection, a foamy virus vector is used which, by means of its exogenous nucleic acid, expresses a secretable anti-interleukin 2 antibody in the target tissue.

2. The foamy virus vector expresses a secretable polypeptide in the target tissue, which polypeptide contains a peptide fragment of the alpha subunit of the acetylcholine receptor and is capable of binding and inactivating antibodies in patients suffering from myasthenia gravis.

Other polypeptides expressed using recombinant foamy virus vectors could be lymphokines, such as interleukin 2, for example, in cells which are neoplastically transformed but prevented from proliferating by chemical or physical means, for the purposes of cancer immunotherapy. In this case, the cells to be used for the immunotherapy are transduced ex vivo with foamy virus vector. Likewise, immunotherapy of cancer can be conducted by in vivo transduction of tumour cells with foamy virus vector as outlined within Example II.

The expression, mediated by foamy virus vector, of one or more interferons in the target tissue is also conceivable as a means of antiviral therapy and/or cancer therapy.

Furthermore, neoplastically transformed cells or cells which are infected with lentiviruses or hepatitis viruses can be therapeutically treated with recombinant foamy virus vectors by the vectors expressing, in the target tissue, a toxin or else a polypeptide which is converted into a cytotoxic polypeptide by the intracellular pathogen or the particular metabolism of the neoplastically transformed cell. Foamy virus vectors could be constructed for expressing ricin A or diphtheria toxin or Staphylococcus aureus enterotoxin B or colicin E, or other toxins. In order to ensure expression of such products which was specific for the cell or organ, foamy virus vectors would be constructed which form the cytotoxic polypeptide under the control of a promoter which was cell-specific or organ-specific.

Other therapeutic proteins which can be expressed endogenously in target cells by recombinant foamy virus vectors are, for example, protease inhibitors against virus proteases of pathogenic lentiviruses or hepatitis viruses. They can also be protease inhibitors against elastase and/or trypsin, and other proteases, which must be inhibited in adult respiratory distress syndrome and emphysema, and in other disease conditions. They can also be proteins such as, for example, tumour necrosis factor (TNF), which can be used with foamy virus vectors for treating cancer. Furthermore, missing tumour-suppressing genes can be expressed with the aid of foamy virus vectors.

A further example of an important application of the foamy virus vector is the use of this vector to transfer the multi-drug resistance gene (MDR) into blood-forming cells in order to protect the bone marrow cells (bone marrow stem cells, CD34-progenitor cells and other haematopoietic cells) during tumour therapy using cytostatic chemotherapeutic agents, or other such agents, which damage the bone marrow.

IV. Foamy virus vectors for homologous recombination with cellular chromosomal DNA Undesirable genes, for example proviral DNA of lentiviruses, amplified oncogenes, genes eliciting hereditary disorders, and other genes, can be inactivated by foamy virus vectors which contain exogenous nucleic acid possessing DNA sequences which are homologous to the undesirable genes. For this purpose, the exogenous nucleic acid of the foamy virus vectors is chosen in such a way that it leads, at high frequency and in a preferred manner, to destruction of the corresponding cellular genes by homologous recombination. However, a defective gene can also be corrected in this way at the gene locus by recombination with the intact gene of the exogenous nucleic acid of the foamy virus vector.

V. Foamy virus vectors for the somatic gene therapy of hereditary diseases

Hereditary diseases, such as, for example, deficiencies in the blood coagulation factors VIII or IX, or adenosine deaminase deficiency, or haemoglobinopathies, or cystic fibrosis, or familial hypercholesterolemia, or hereditary emphysema, or Duchenne muscular dystrophy, or other hereditary diseases, can be treated by transferring the appropriate, correct gene into somatic cells using foamy virus vectors.

VI. Foamy virus vectors for treating cardiovascular diseases

Recombinant foamy virus vectors can be constructed whose exogenous nucleic acid comprises one or more genes for expressing polypeptides which have the effect of regulating blood pressure. Thus, the polypeptides can, for example, be regulatory atrial natriuretic peptides which act in a transdominant negative manner. They can be polypeptides for binding and inactivating the circulating ANP (atrial natriuretic peptide) or ANF (atrial natriuretic factor). These polypeptides can, for example, be antibody-like proteins, or they can, for example, be soluble receptor derivatives of ANP or ANF-binding receptors. They can be inhibitors of renin, or inhibitors of the angiotensin-converting enzymes, to name a few examples.

The genes of the exogenous nucleic acid in foamy virus vectors can also encode products which inhibit the development of arteriosclerosis or other cardiovascular diseases. These products can be substances which inhibit the proliferation of endothelial cells or cells of the smooth musculature, e.g. antisense RNA against c-myb mRNA or against TGF-β mRNA, to name examples.

In this connection, the therapeutic product formed by a foamy virus vector can also be the LDL receptor.

Foamy virus vectors can be constructed for expressing antisense RNA or ribozyme RNA which is directed against adhesive proteins, such as, for example, E selectin or P selectin. Besides inhibiting the translation of the mRNA of selected adhesive proteins by complementary RNA, the foamy virus vectors can also contain exogenous nucleic acid for expressing polypeptides which are secreted into the blood circulation and which block the interaction of blood cells with each other (e.g. blood platelet aggregation), or of blood cells with endothelial cells, by binding selectively to adhesive proteins, such as, for example, E selectin or P selectin. The blocking of adhesive proteins in the blood and on endothelial cells is of importance as a therapeutic principle in regard to pathological changes of the blood vessels and in regard to inflammatory diseases.

VII. Foamy virus vectors for diagnostic applications

The exogenous nucleic acid of recombinant foamy virus vectors can comprise a gene or gene fragment which is activated in the cell by a substance which is to be detected and thereby, specifically and with an amplifiable signal, renders the substance detectable in a highly sensitive manner.

The detection of a viral or bacterial transactivator protein in cells from biopsy material, body fluids, cell lines, production cell lines, or other cells, may be mentioned here by way of example. By means of coupling a transactivatable gene sequence to a downstream reporter gene such as, for example, luciferase or β-galactosidase, or a peroxidase, such transactivator proteins, which may themselves confirm the existence of an infection, can be detected sensitively by a foamy virus vector in the cells under investigation.

VIII. Construction of foamy virus vectors by the in-vitro recombination of nucleic acids The infectious molecular clone pHSRV-2 (FIG. 1) is a derivative of pHSRV-1. pHSRV-1 was obtained by cDNA cloning and cloning of non-integrated viral DNA of human foamy virus (A. Rethwilm et al., Gene 59, 19–28 (1987), A. Rethwilm et al., Nucleic Acids Res. 18, 733–738 (1990)). In pHSRV-1 approx. 500 bp are deleted from the U3 region of the 5'LTR and approx. 350 bp are deleted from the U3 region of the 3'LTR (A. Rethwilm et al., unpublished). In pHSRV-2 500 bp are deleted in both LTRs. This was facilitated by replacing a AflII/XbaI fragment in the 3'LTR of pHSRV-1 by the corresponding fragment of the 5'LTR. Both plasmids give rise to infectious virus after transfection of susceptible cells. To obtain the pFOV vectors depicted in FIG. 2–7 deletions in the bel-2/bel-3 were introduced with the aid of restriction endonucleases AccI and HindIII between the nucleotide positions 10420 and 10844, respectively, of pHSRV-2 (FIG. 1). A multiple cloning sequence having the cleavage sites for EcoRV, SmaI and NruI, was inserted into this deletion in pFOV-1. In pFOV-1 a foreign DNA sequence is expressed as a fusion protein to a c-terminal truncated Bet protein. In pFOV-2 an internal ribosomal landing pad was inserted into the AccI/HindIII deletion. In addition, two stop codons have been introduced into the bel-2 open reading frame (G. Baunach et al., J. Virol. 67 5411–5418, (1993)). pFOV-3, pFOV-5 and pFOV-6 are derivatives of pFOV-2, in which the splice donor site in the bel-1 open reading frame (pFOV-3), the splice acceptor site of the bel-2 open reading frame (pFOV-5), or both 8pFOV-6) have been mutagenised. pFOV-2, pFOV-3, pFOV-5, and pFOV-6 give rise to authentic protein encoded by a foreign DNA inserted into these vectors.

These vectors are replication-competent and were used successively for expressing exogenous nucleic acid (e.g. for expressing the CAT gene (chloramphenicol acetyltransferase)).

The vector pFOV-4 (FIGS. 1 and 5) was prepared by deleting the proviral DNA between the EcoRI (nucleotide position 9529) and Hind III (nucleotide position 10844) restriction sites. This foamy virus vector is replication-incompetent.

IX. Production of foamy virus vectors

The replication-competent foamy virus vectors, such as, for example, pFOV-1 to pFOV-3, can be propagated in cell lines such as, for example, HEL 299 (ATCC CCL 137) human embryonic lung fibroblast cells, BHK-21 (C-13) (ATCC CCL 10) hamster kidney cells, CF2TH (ATCC CRL 1430) canine thymus cell line, MRC5 (ATCC CCL 171) human lung cell line, CHO Chinese hamster ovary cell line, VERO (ATCC CCL 81) African green monkey kidney cell line, 3TS-TK⁻ (ATCC CCL 92) mouse fibroblast cell line, and other cell lines, or in primary tissue cultures or infected animals. The cell culture supernatants or fluids from infected animals which contain the infectious foamy virus vector particles can be employed for infecting target cells.

Replication-incompetent foamy virus vectors are produced using recombinantly altered packaging cell lines. The replication-incompetent foamy virus vector possesses gene deletions which rule out replication of the vector in a somatic cell which is not infected with replication-competent foamy viruses. In addition to the bel genes, these gene deletions can encompass the gag gene region and/or the pol gene region and/or the env gene region.

The proteins of the deleted gene(s) are formed by one or more foamy virus genes which have been transfected, for example by conventional gene transfer (e.g. electroporation or CaPO₄ precipitation), into a packaging cell line. A feature of the packaging cell line is that it expresses one or more foamy virus proteins, such as the gag, pol and/or env proteins, which enable it to pack the genomic RNA of the vector, which also includes the exogenous nucleic acid, into infectious foamy virus particles, since these proteins are provided in trans in the packaging cell line. Infectious, but replication-incompetent, foamy virus vector particles are produced in this way for safety reasons. The packaging cell line can be one of the abovementioned cell lines or, alternatively, another suitable cell line.

Alternatively, the foamy virus vector can also be isolated as pure proviral DNA from a suitable cloned plasmid DNA and introduced, with or without formulation auxiliaries such as, for example, cationic lipids or proteins, which represent a carrier, into the target cells, for medicinal or diagnostic applications, by injection, electroporation, particle bombardment, or similar techniques.

X. Foamy virus vectors for generating tissue cultures and animals with particular physiological properties (cell and animal models) for biological, pharmacological and medical investigations Cells of tissue cultures (ex vivo) or tissue cells in animals (in vivo) can be transduced with foamy virus vectors in order to elicit expression of particular genes in these cells using the vector. By these means, a particular physiological condition, a particular metabolic result, or a particular biochemical property of cells, can be produced ex vivo or in vivo. These cells which have been altered in this way can be of great value for physiological, pharmacological or medical investigations. They can, for example, be tested ex vivo or in vivo for determining the function of a gene or for determining the effect of an active compound or of a medicament which is under examination. Furthermore, such transduced cells (cells which have been genetically altered by the vector) can be an exceptionally valuable aid in searching, by ex vivo cell tests or in vivo animal experiments, for active compounds (substances prepared chemosynthetically or biologically) which are suitable for further development as medicaments (active compound screening). Concrete examples are provided by the use of the vector to transfer oncogenes like c-myc, ras, bcr-abl, or HIV-tat into selected animal organs in order to study the oncogenic potential of the oncogenes in the genetically altered cells, to study oncogene-dependent tumorigenesis, and to test active compounds in vivo for their ability to inhibit tumorigenesis.

A bel-1 expressing packaging cell lines can be used to produce pFOV-4-vector that contains a HIV-LTR-reporter gene construct. This vector infects primary human macrophages, neuronal cells and other somatic cells. Such transduced macrophages or other primary cells can be used for diagnostic purposes as outlined in Example VII for sensitive HiV detection by co-cultivation with samples to be analyzed for HIV contamination. Because, there are HIV isolates of clinical relevance, that are restricted to a narrow host range and can therefore not cultivate din peripheral blood lymphocyte samples.

Such pVOF-4 transduced macrophages or other cells are also a HIV inhibiting substances. Furthermore, if the reporter gene of pFOV-4 is replaced by potential suicide genes like Staphylococcus enterotoxin B, or ricin A, or other genes encoding a cytotoxic product, pFOV-4 is used to screen for suicide genes activated upon HIV infection of such primary somatic cells.

Furthermore, human cell adhesion proteins (selectins) can be expressed, using foamy virus vectors, in various somatic animal cells, thereby making it possible to screen for antiflammatory, selectin-binding, active compounds in the animal (e.g. mouse). These are two examples of test models for "molecular pharmacology", using human proteins in animals, which are being realised with the aid of the foamy virus vectors.

Figure 1:
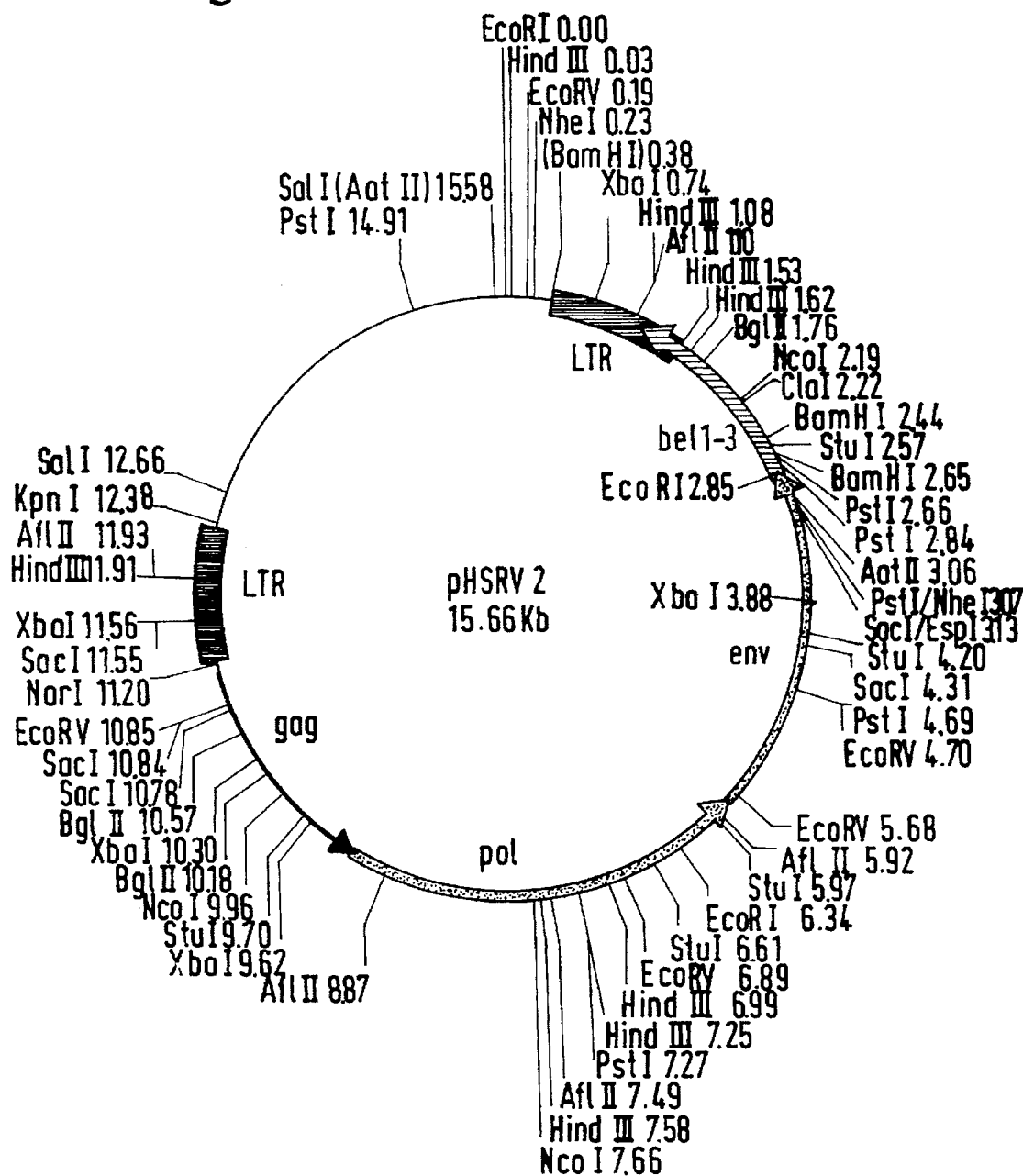
FIG. 1
Figure 2:
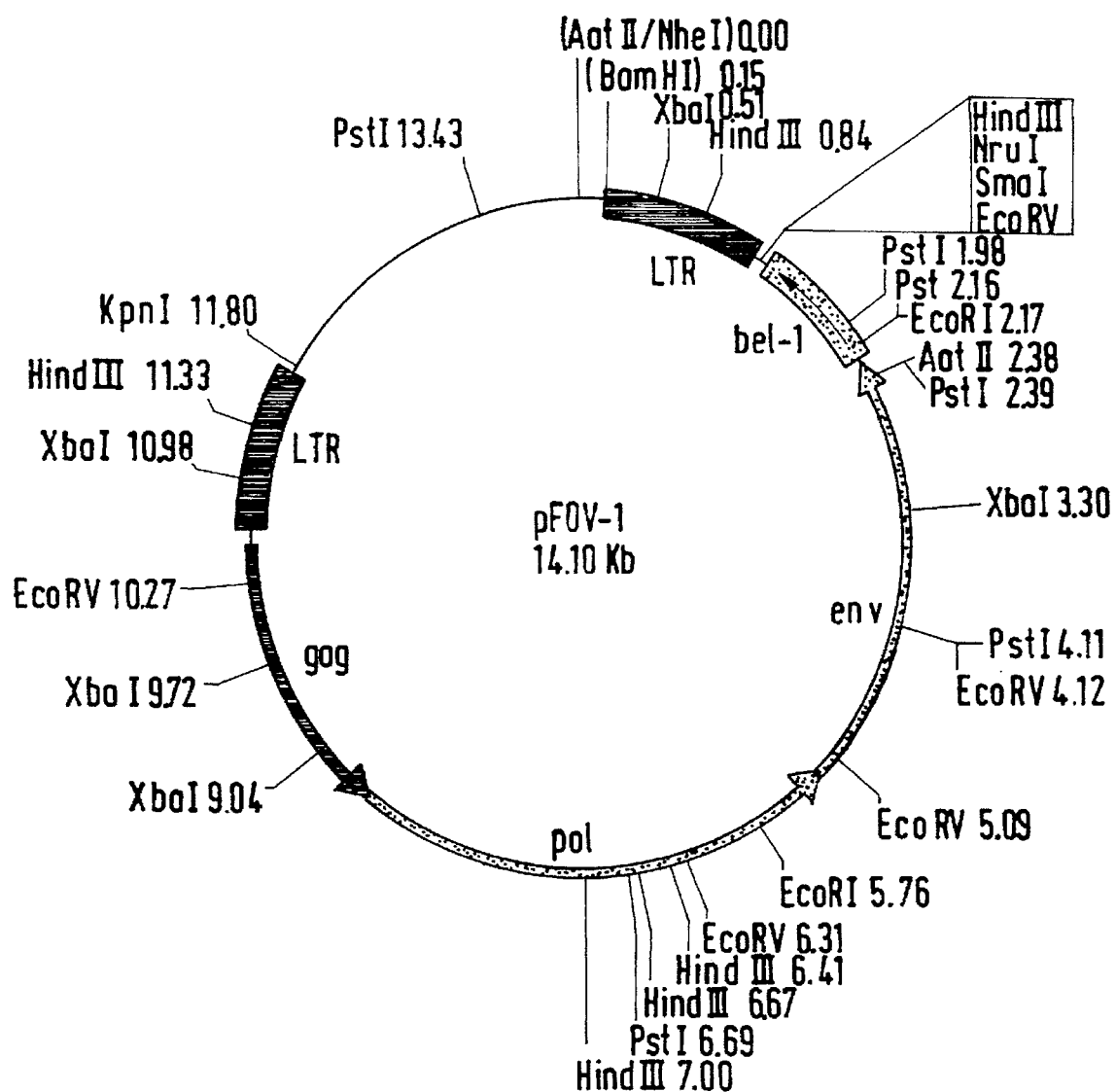
Figure 3:
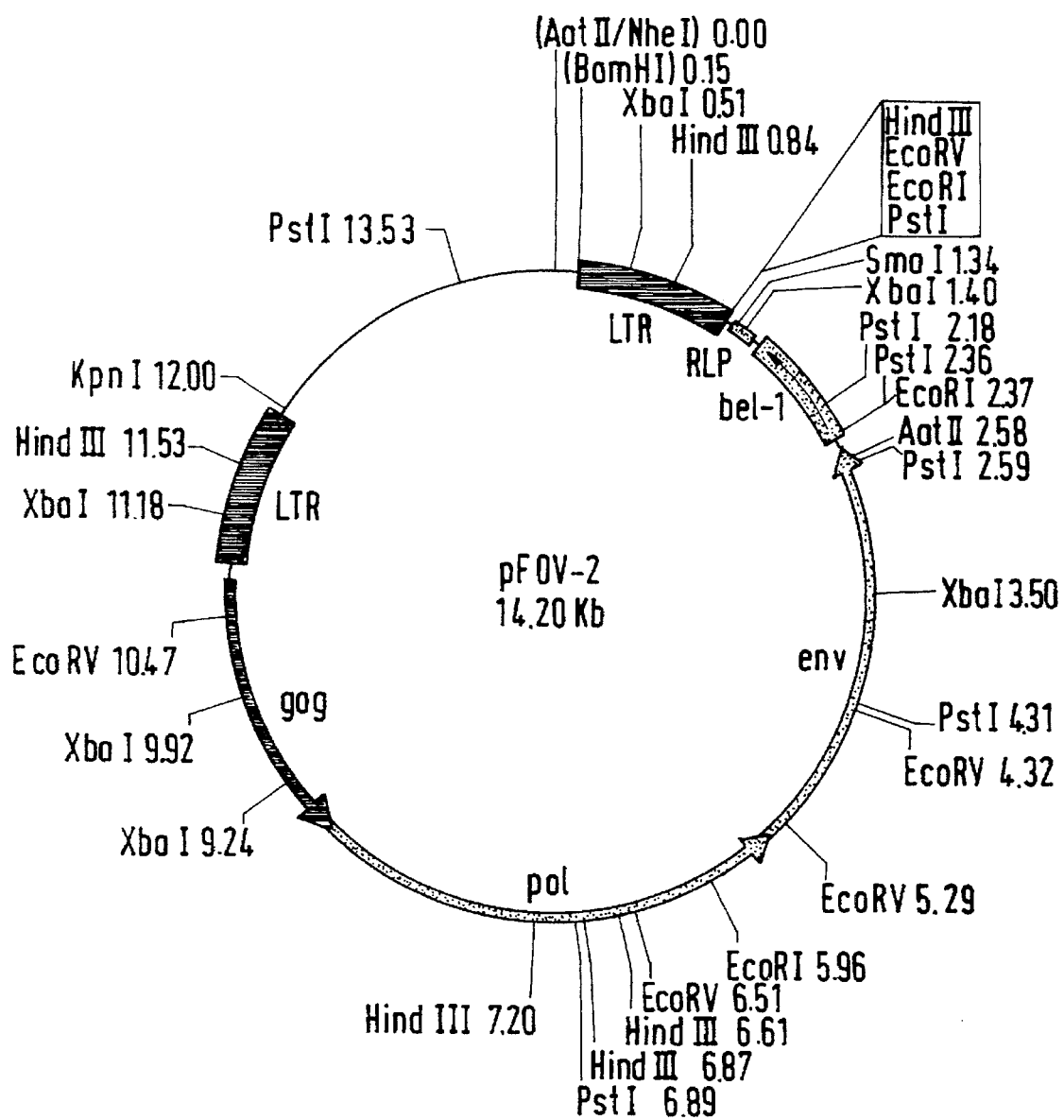
Figure 4:
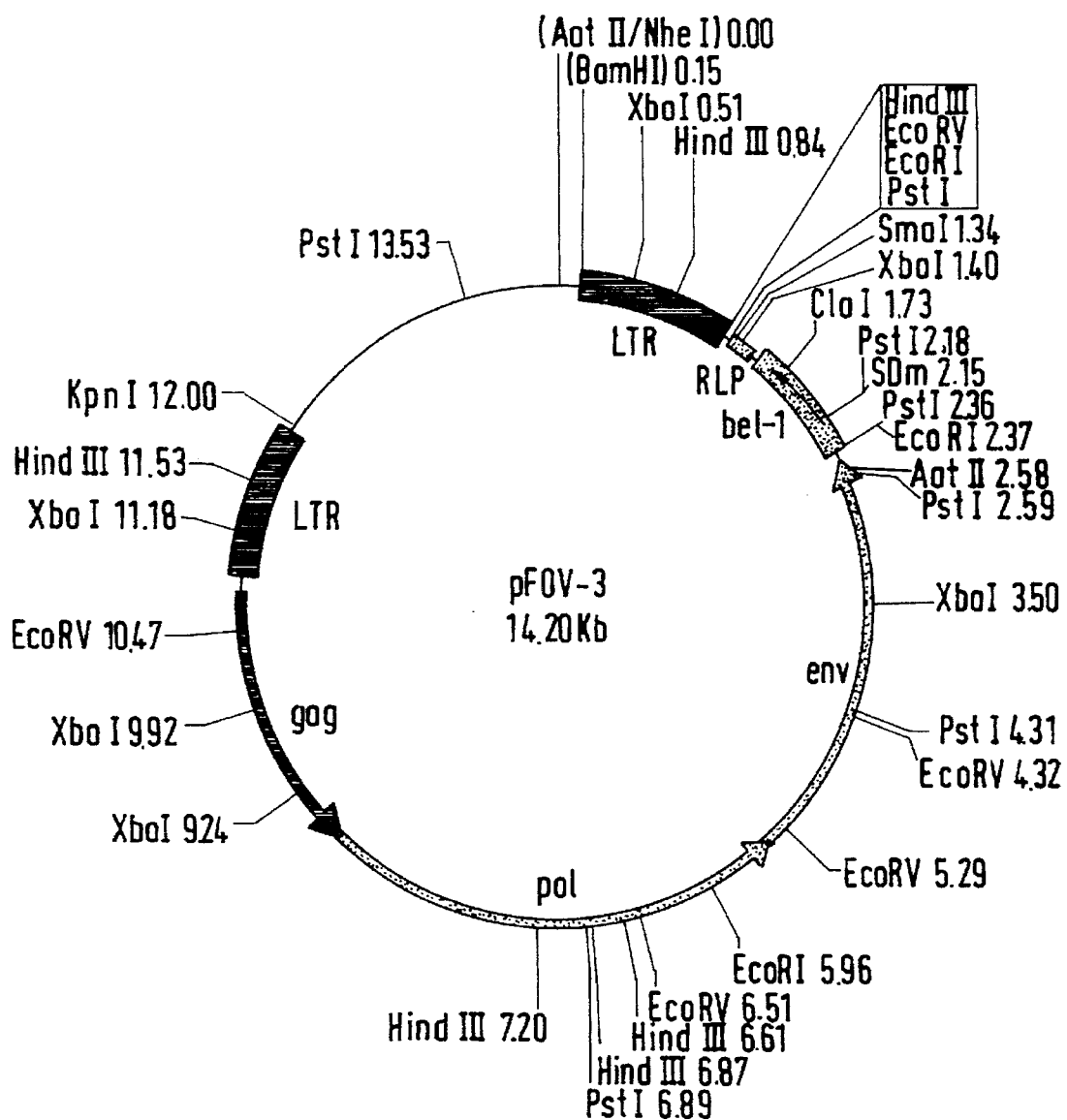
Figure 5:
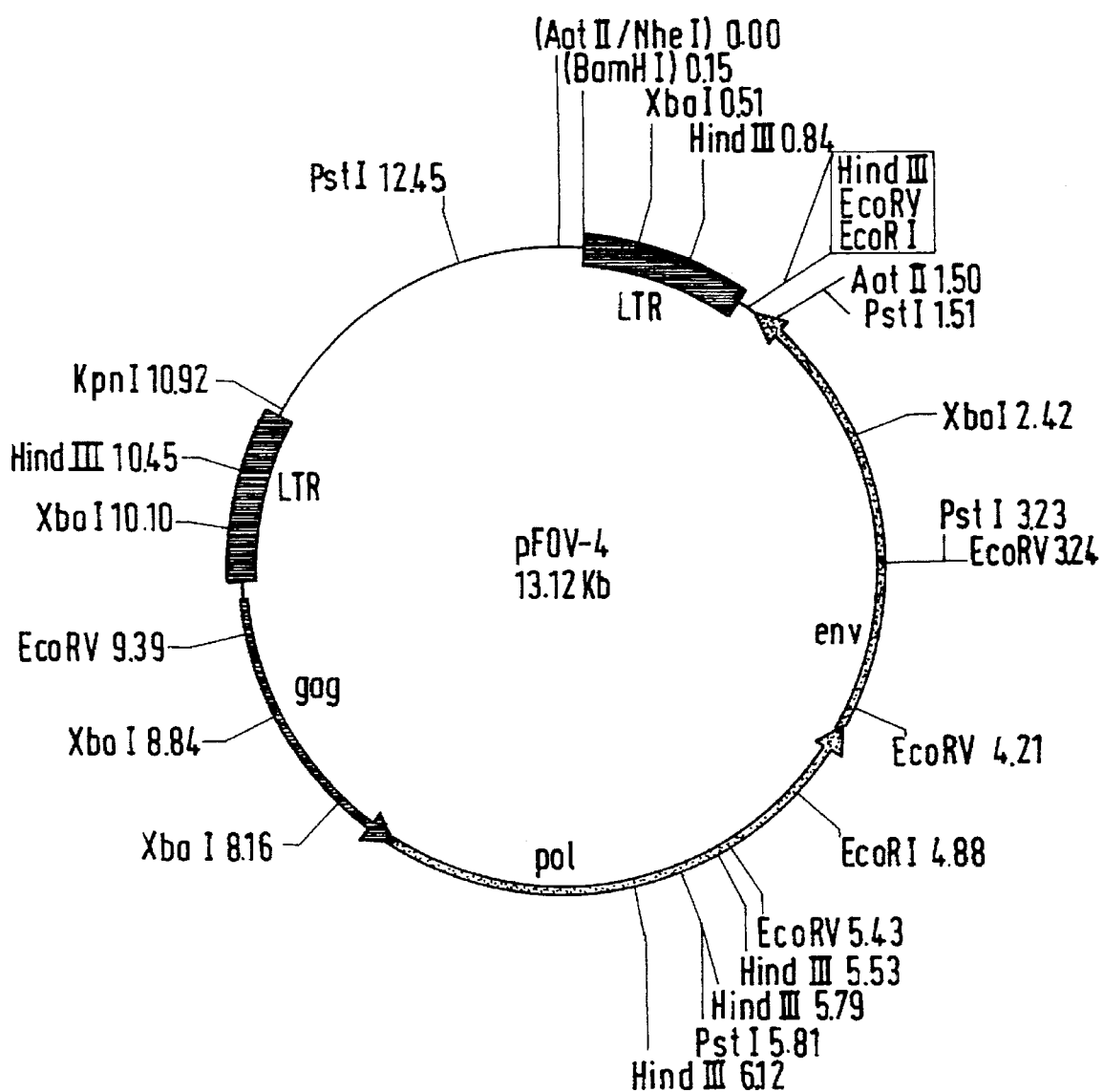
Figure 6:
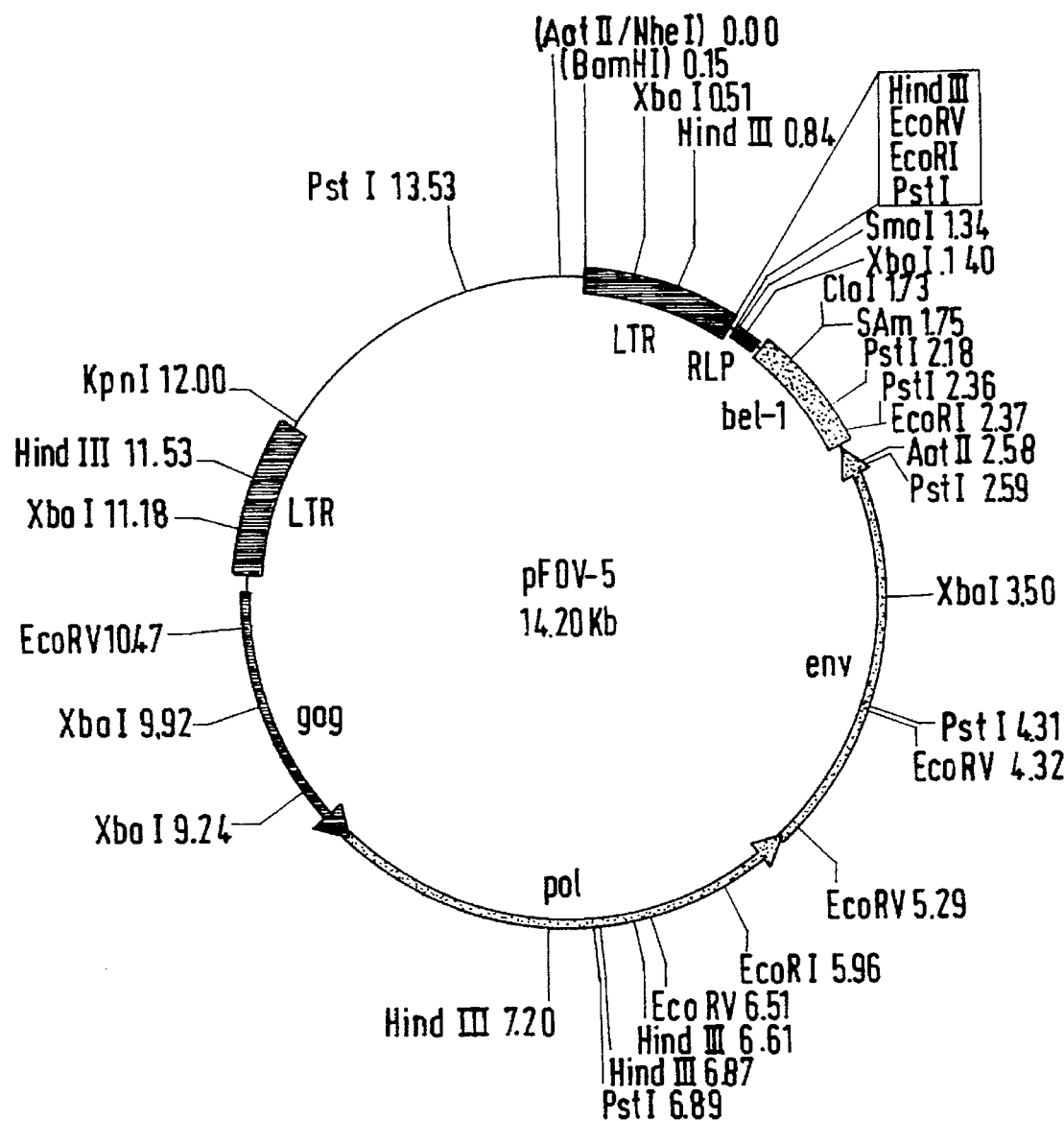
Figure 7:
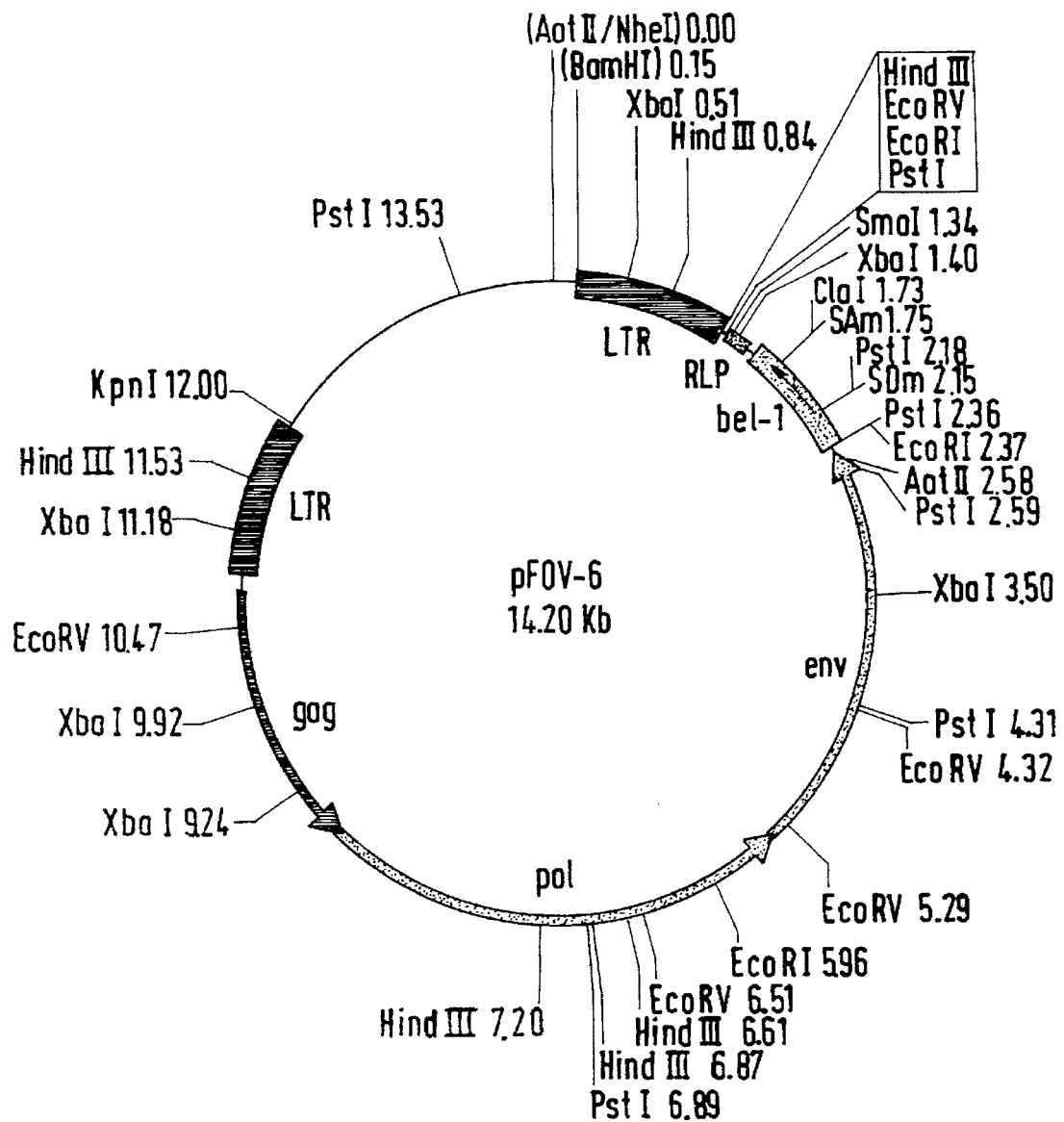

Diagrammatic representation of the genomic structure of pHFV (infectious proviral DNA of human spumaretrovirus pHSRV-2) and of foamy virus vectors pFOV-1, pFOV-2 and pFOV-3, which are derived from it by deletions at the AccI and Hind III cleavage sites (nucleotide positions 10420 and 10844, respectively). The replication-incompetent vector pFOV-4 possesses a larger deletion between EcoR I (nucleotide position 9529) and Hind III (nucleotide position 10844). Multiple cloning sites, e.g. the EcoR V, Sma I and Nru I cleavage sites shown here, were inserted in place of the deletions.

FIG. 2

Restriction map of the foamy virus vector pFOV-1.

FIG. 3

Restriction map of the foamy virus vector pFOV-2.

FIG. 4

Restriction map of the foamy virus vector pFOV-3.

FIG. 5

Restriction map of the foamy virus vector pFOV-4.

FIG. 6

Restriction map of the foamy virus vector pFOV-5.

FIG. 7

Restriction map of the foamy virus vector pFOV-6.

We claim:

1. Infectious or non-infectious DNA of human spumaretrovirus pHSRV-1 or pHSRV-2 comprising an internal deletion, that spans a portion of each of the bel-1, bel-2 and bel-3 genes or an internal deletion that spans a portion of each of the bel-2 and bel-3 genes, but not the bel-1 gene.

2. Infectious or non-infectious DNA according to claim 1, wherein said deletion spans a portion of each of the bel-2 and bel-3 genes, but not the bel-1 gene.

3. Infectious or non-infectious DNA according to claim 2, wherein said deletion adjoins the bel-1 gene and is approximately 420 base pairs in the 3' direction.

4. Infectious or non-infectious DNA according to claim 3, wherein said deletion is between nucleotide positions 10420 and 10844 of pHSRV-2.

5. Infectious or non-infectious DNA selected from the group consisting of pFOV-1, pFOV-2, pFOV-3, pFOV-4, pFOV-5 and pFOV-6.

6. Infectious or non-infectious DNA of human spumaretrovirus pHSRV-1 or pHSRV-2 comprising a deletion into which there has been inserted an exogenous nucleic acid, said deletion spanning a portion of each of the bel-1, bel-2 and bel-3 genes or spanning a portion of each of the bel-2 and bel-3 genes, but not the bel-1 gene.

7. Infectious or non-infectious DNA according to claim 6, wherein said deletion spans a portion of each of the bel-2 and bel-3 genes, but not the bel-1 gene.

8. Infectious or non-infectious DNA according to claim 6, wherein said exogenous nucleic acid comprises at least one complete gene which encodes a polypeptide.

9. A eukaryotic cell line, or a recombinant eukaryotic cell line, producing infectious or non-infectious DNA according to claim 6.

10. A human or animal somatic cell transfected with infectious or non-infectious DNA according to claim 6 and expressing said exogenous nucleic acid.

11. Infectious or non-infectious DNA according to claim 7, wherein said deletfon adjoins the bel-1 gene and is approximately 420 base pairs in the 3' direction.

12. Infectious or non-infectious DNA according to claim 11, wherein said deletion is between nucleotide positions 10420 and 10844 of pHSRV-2.

13. Infectious or non-infectious DNA according to claim 8, wherein said polypeptide is a human humoral or cellular antigen.

14. Infectious or non-infectious DNA according to claim 8, wherein said polypeptide is selected from the group consisting of antisense RNA, ribozyme RNA or decoy RNA.

15. Infectious or non-infectious DNA according to claim 8, wherein said polypeptide is capable of inhibiting tumor formation.

16. Infectious or non-infectious DNA according to claim 8, wherein said polypeptide is a product that is either defectively produced by a target organism or is not produced at all by said target organism.

17. Infectious or non-infectious DNA of human spumaretrovirus pHSRV-1 or pHSRV-2 comprising a deletion into which there has been inserted an exogenous nucleic acid, said deletion being in the bel-1, bel-2 or bel-3 genes.

18. A eukaryotic cell line, or a recombinant eukaryotic cell line, producing infectious or non-infectious DNA according to claim 17.

19. A human or animal somatic cell transfected with infectious or non-infectious DNA according to claim 17 and expressing said exogenous nucleic acid.

* * * * *

UNITED STATES PATENT AND TRADEMARK OFFICE
CERTIFICATE OF CORRECTION

PATENT NO. : 5,646,032
DATED : July 8, 1997
INVENTOR(S) : ter Meulen, et al.

It is certified that error appears in the above-indentified patent and that said Letters Patent is hereby corrected as shown below:

Col. 10, line 63   Delete " deletfon " and substitute -- deletion --

Signed and Sealed this

Twenty-first Day of April, 1998

Attest:

BRUCE LEHMAN

Attesting Officer

Commissioner of Patents and Trademarks